United States Patent [19]

Bowers-Irons et al.

[11] Patent Number: 5,030,426

[45] Date of Patent: * Jul. 9, 1991

[54] BIOMINING OF GALLIUM AND GERMANIUM CONTAINING ORES

[75] Inventors: Gail L. A. Bowers-Irons, Salt Lake City; John R. Pease, Kearns; Quynh K. Tran, Salt Lake City; Tracy Gibb, Salt Lake City; Robert J. Pryor, Salt Lake City; Sandra Haddad, Centerville, all of Utah

[73] Assignee: Technical Research, Inc., Salt Lake City, Utah

[*] Notice: The portion of the term of this patent subsequent to Jul. 9, 2008 has been disclaimed.

[21] Appl. No.: 401,076

[22] Filed: Aug. 31, 1989

Related U.S. Application Data

[63] Continuation-in-part of Ser. No. 372,058, Jun. 27, 1989.

[51] Int. Cl.$^5$ .................. C22B 13/00; C22B 25/00; C22B 41/00; C22B 58/00
[52] U.S. Cl. .................... 423/98; 423/109; 423/131; 423/DIG. 17; 435/262
[58] Field of Search ......... 423/131, 98, 109, DIG. 17; 75/101 R, 121, 743; 435/262

[56] References Cited

U.S. PATENT DOCUMENTS

| | | | |
|---|---|---|---|
| 3,272,621 | 9/1966 | Zajic | 423/DIG. 17 |
| 4,571,387 | 2/1986 | Bruynesteyn et al. | 435/262 |
| 4,728,082 | 3/1988 | Emmett, Jr. et al. | 266/168 |
| 4,732,608 | 3/1988 | Emmett, Jr. et al. | 75/101 R |
| 4,758,345 | 7/1988 | Francis et al. | 210/912 |

OTHER PUBLICATIONS

Use of Micro-Organisms for the Recovery of Metals, by Tuovinen and Kelly, International Metallurgical Reviews, vol. 19, 1974.
"The Separation of Gallium and its Colorimetric Determination by Means of Quinalizarin", by H. Willard, et al. (1937).
"The Chemistry of Gallium", by Sheka, et al. (Elsevier Publishing Co. 1966).
"The Bacterial Leaching of Metals from Ores", by Karaivko, et al. (Technicopy Limited, 1977).
"Analytical Chemistry of Gallium", by Dymov and Savostin (Ann Arbor Science Publishers, 1970).
"Acid-Bacterial and Ferris Sulfate Leaching of Pyrite Single Crystals", by Keller, et al. (24 Biotech. and Bioeng., 1982, pp. 83-96).
"Studies on the Chemoautotrophic Iron Bacterium Ferrobacillus ferrooxidans", by Silverman, et al, 1958.
"Kinetics of Bio-chemical Leaching of Sphalerite Concentrate", by Chaudhury, et al. (16B Metallurgical Transactions, Dec. 1985, pp. 667-670).
"Microorganisms in Reclamation of Metals", by Hutchins, et al. (40 Ann. Rev. Microbiol., 1986, pp. 311-336).
"Oxidation of Gallium Sulfides by Thiobacillus ferrooxidans", by A. Torma (24 Can J. Microbiol., 1978, pp. 888-891).
"Biological Leaching: A New Method For Metal Recovery", (B.C. Research).

(List continued on next page.)

Primary Examiner—Michael L. Lewis
Assistant Examiner—Steven Bos
Attorney, Agent, or Firm—Trask, Britt & Rossa

[57] ABSTRACT

Disclosed is a high temperature process (e.g. >60° C.) for leaching selected metal compounds e.g. gallium or germanium from ore containing those compounds. The method includes placing the ore into a culture medium containing bacteria. Bacteria capable of leaching the metal compounds from the ore leach the metals from the ore. The bacteria preferably used will be bacteria ATCC 53921 and mutations and recombinants thereof. The ore is generally crushed to between 20 and −400 mesh before placement into the culture medium containing bacteria.

14 Claims, 12 Drawing Sheets

OTHER PUBLICATIONS

"Ore Leaching by Bacteria", by Lundgren, et al. (34 Ann Rev. Microbiol, 1980, pp. 263-283).

"Bacterial Leaching", by C. Brierley (CRC Critical Reviews in Microbiology, Nov. 1978).

"Continuous Bacterial Coal Desulfurization Employing Thiobacillus Ferrooxidans", by Myerson, et al. (26 Biotech. and Bioeng., 1984, pp. 92-99).

"Development of a Continuous Process for Metal Accumulation by Zoogloea ramigera", by Norberg, et al. (26 Biotech. and Bioeng., 1984, pp. 265-268).

"Biosorption of Uranium and Lead by Streptomyces Longwoodensis", by Friis, et al. (28 Biotech. and Bioeng., 1986, pp. 21-28).

"Accumulation of Heavy-Metal Ions by Zoogloea ramigera", by Norberg, et al. (26 Biotech. and Bioeng., 1984, pp. 239-246).

"Microbiological Mining", by C. L. Brierly (1982).

"Wastewater Engineering: Treatment, Disposal, Reuse" (McGraw-Hill; 2nd edition, pp. 494 and 497).

"Biologically Mediated Inconsistencies in Aeration Equipment Performance", by Albertson, et al. (47 Jr. WPCF, No. 5, May 1975, pp. 976-988).

The Dorrco Technical Manual, sec. 32, Dec. 1951.

"Bioaccumulation of Germanium by Pseudomonas putida in the presence of Two Selected Substrates", by Chmielowski, et al. (Applied and Envir. Microbiology, May 1986, pp. 1099-1103).

BIOMINING OF GALLIUM AND GERMANIUM CONTAINING ORES

This invention was made with Government support under Contract No. F33615-87-C-5303 awarded by the United Stated Air Force. The Government has certain rights in this invention.

RELATED APPLICATIONS

This application is a continuation-in-part of U.S Ser. No. 07/372 058 filed on June 27, 1989, the contents of which are incorporated by this reference.

BACKGROUND OF THE INVENTION

Field

This invention is directed to a biological process for use in removing metallic components from ores by biological techniques. The invention is more particularly directed to the extraction of gallium or germanium from gallium or germanium containing ores.

State of the Art

In the United States, gallium is generally produced as a byproduct of the Bayer process for producing alumina from bauxite and from zinc processing residues. Recently the Apex St. George, Utah mine began operation which recovers gallium and germanium as main products.

The Apex mine holds an ore body which requires a unique recovery process. This ore body is an admixture of waste, dolomite and silica. Valuable elements are found in the jarosite ($KFe_3(SO_4)_2(OH)_6$), geothite ($Fe_2O_3 \cdot xH_2O$) and quartz ($SiO_2$) making traditional separation of the mineral from the waste rock very difficult.

The gallium and germanium host materials are believed to be geothite, limonite ($2Fe_2O_3 \cdot H_2$), hematite ($Fe_2O_3$), jarosite, azurite ($Cu_3(CO_3)_2(OH)_2$), malachite ($Cu_2CO_3(OH)_2$), conichalcite ($CaCu(AsO_4)(OH)$) and minor amounts of other metal carbonates, oxides, sulfates, and arsenates. As used herein, "host materials" refer to those ores or similar compounds which have gallium or germanium imbedded therein. Most of the copper-rich ore was removed during previous mining operations and the iron-rich minerals that contain most of the germanium and gallium were rejected as waste. The gallium is generally concentrated in the jarosite.

The Apex mine uses a hydrometallurgical extraction process to recover the metals from the minerals. A "trade-off" exists between necessary leach extraction, the feasibility of separations, corrosiveness to the equipment, and cost.

The process involves leaching with one or more purification steps, and a winning or recovery step. The leaching vessels are arranged in a countercurrent manner to give both good extraction and maximum utilization of reagents. A 40% sulfur dioxide solution at 85% reacts with iron oxide as shown in the following equation:

$$2FiOOH + SO_2 + 2H^+ = 2Fe^{30+} + SO_4 + 2H_2O \qquad (1)$$

A solution of gallium, copper, zinc, arsenic in small quantities and large amounts of iron and magnesium results. Copper is removed before the target elements become accessible.

The solution containing the gallium, zinc, arsenic, iron and magnesium is subjected to solvent extraction. The gallium and zinc are transferred by an organophosphorus-kerosene solvent to a fresh sulfuric acid solution.

$$Ga^{3}O_3 + 3HX_{org} = GaX_{3org} + 3H^+ \qquad (2)$$

Gallium is precipitated by partial neutralization with ammonia after which the precipitate is redissolved and purified.

$$GaCl_3 + 3NH_3 + 3H_2O = Ga(OH)_3 + 3NH_4Cl \qquad (3)$$

Gallium metal is then produced in small electrowinning cells.

Calcium fluoride with hydrogen sulfide precipitates germanium. This produces hydrogen fluoride which removes the germanium from the silicates in which it is found.

Bacteria (i.e. *Thiobacillus ferrooxidans* and *Ferrobacillus ferrooxidans*) have also been used to extract gallium compounds from gallium containing ore.

As reported in Lundgren et al., "Ore Leaching by Bacteria," *Ann Rev. Microbial*, 34: 63–83 (1980), *Thiobacillus ferrooxidans* has been used to oxidize gallium sulfide ($Ga_2S_3$) to gallium sulfate ($Ga_2(SO_4)_3$). Torma in "Oxidation of gallium sulfides by *Thiobacillus ferrooxidans*", *Can J. Microbial*, 24: 888–891 (1978), disclosed a method for biomining/bioleaching/ biostabilization by bacterium involving inoculating a quantity of gallium-bearing chalcopyrite concentrate and 70 ml iron-free nutrient medium with prepared *T. ferrooxidans*. The system is aerated with carbon dioxide ($CO_2$)-containing air. Distilled water is added to compensate for evaporation, and the pH is maintained at 1.8. The temperature of the reaction is typically 35° C.

*The Bacterial Leaching of Metals From Ores*, written by G. I. Karaivko, et al. (1977), discloses the use of *T. ferrooxidans* in leaching non-ferrous metals and sulfides. This article notes that *T. ferrooxidans* may be used to leach rare metals such as gallium from the crystal structure of many sulfides and non-ferrous metals. The authors suggest a methodology for leaching non-ferrous metals in vats using *T. ferrooxidans*. The method emphasizes the need for proper aeration, optimal mesh size of ore, pH at about 2.8, and a suggested reaction temperature of approximately room temperature (26° C.).

These and other writings indicate an established study of bioleaching of iron- and sulfur-containing ores, but investigation has been done almost exclusively through the use of Thiobacillus species, particularly *T. ferrooxidans*.

For example, bioleaching of copper from chalcopyrite containing ore is described in U.S. Pat. No. 4,571,387 to Bruynsteyn, et al. the contents of which are hereby incorporated by this reference. This patent discloses a process for leaching particular metals from ores using sulfide oxidizing bacteria.

"Studies on the Chemoautotrophic Iron Bacterium *Ferrobacillus ferrooxidans*" by Silverman, et al. (1959) discusses a method for culturing chemoautotrophic bacterium such as Gallionella, *T. ferrooxidans*, and *F. ferrooxidans*.

"Microorganisms in Reclamation of Metals" by Hutchins, et al. (40 *Ann. Rev. Microbiol.* 1986, pp. 311–36), describes various methods of leaching metals from ores using acidophilic iron-oxidizing bacteria. Hutchins further discusses the characteristics of many bacterial forms capable of effectuating bioleaching. Reference is made to bioleaching of $Ga_2S_3$ by *T. ferrooxidans*.

"Biological Leaching: A New Method For Metal Recovery" (B.C. Research; Vancouver, B.C.) provides a general discussion of bioleaching of sulfides in industrial and commercial applications.

"Ore Leaching By Bacteria" by Lundgren, et al. (34 Ann. Rev. Microbiol. 1980, pp. 263-83) details the chemical mechanisms of bioleaching metals from insoluble minerals.

"Bacterial Leaching" by C. Brierley (CRC Critical Reviews in Microbiology, Nov. 1978) discusses industrial applications of bioleaching, with particular emphasis on uranium and copper recovery. Details are provided regarding bacterial efficacy parameters.

"Continuous Bacterial Coal Desulfurization Employing Thiobacillus ferrooxidans" by Myerson, et al. (26 Biotech. and Bioeng. 1984, pp92-99) discusses the increase in bioleaching activity with increase in surface substrate availability.

"Microbiological Mining" by C. L. Brierly (1982) discusses the role played by T. ferrooxidans in leaching copper from low-grade ore on an industrial scale.

"Wastewater Engineering: Treatment, Disposal, Reuse" (McGraw-Hill; 2d Ed, pp. 494-497) discloses "Biologically Mediated Inconsistencies in Aeration Equipment Performance" by Albertson, et al. (47 Jr. W.P.C.F. No. 5, May 1975, pp. 976-988) provides an evaluation of aeration devices used in biological systems.

The Dorrco Technical Manual, Sec. 32, describes the operation of an agitator—slurry mixer.

"The Bacterial Leaching of Metals from Ores" by Karaivko, et al. (Technicopy Limited, 1977) provides a treatise on bioleaching methodologies, and makes reference to the aqueous migration of gallium in relation to pH values in bioleaching processes.

The use of T. ferrooxidans and F. ferrooxidans has not proven economically useful in extracting gallium and germanium from the ores contained at mines such as the Apex. These bacteria are insufficient to extract the metals at effective (e.g. 95% recovery) levels.

SUMMARY OF THE INVENTION

The invention includes a biological process for leaching gallium, germanium, or mixtures thereof at elevated temperatures from a conglomeration of materials, such as ores containing those compounds. The method generally involves comminuting or crushing the ore and placing the crushed ore into a culture media containing selected bacteria. The selected bacteria are capable of leaching the gallium and germanium compounds from the ore. The process requires an amount of time sufficient to allow the bacteria to leach the metals from the ore into the culture medium The bacteria may be a mixture of different species of bacteria. Bacteria preferably used are those deposited with ATCC identified as ATCC Deposit No. 53921 or mutations or recombinants thereof. The organisms denominated as bacteria ATCC 53921 differ from Thiobacillus and other species which have been used in other bioleaching processes. Bacteria ATCC 53921 exhibit a greater affinity for gallium and germanium than Thiobacillus, exhibit an affinity for arsenic, operate at lower pH values, and operate at a wider range of temperatures (room temperature to 90° C). Furthermore, T. ferrooxidans is generally unaffected by the presence of copper, which exhibits a "poisoning" effect on bacteria ATCC 53921.

The ore is generally crushed to between 20 and −400 mesh, although it need not be crushed at all. All references to mesh, unless otherwise denominated, are to "Tyler mesh." The process is typically conducted at a temperature of about 25° to about 85° centigrade and at a pH of between 1.0 and 2.5. The process is generally more effective at higher temperatures.

Air containing oxygen, carbon dioxide or combinations thereof may be diffused or sparged through the culture medium, bacteria, and ore although this step is not essential to the practice of the invention.

In an alternative embodiment of the invention, the bacteria is a recombinant bacteria containing DNA derived from bacteria ATCC 53921 or mutations thereof. In another alternative embodiment, the bacteria used to bioleach the gallium or germanium contains DNA derived from bacteria ATCC 53921.

DETAILED DESCRIPTION OF THE PREFERRED EMBODIMENTS

Figure 1:
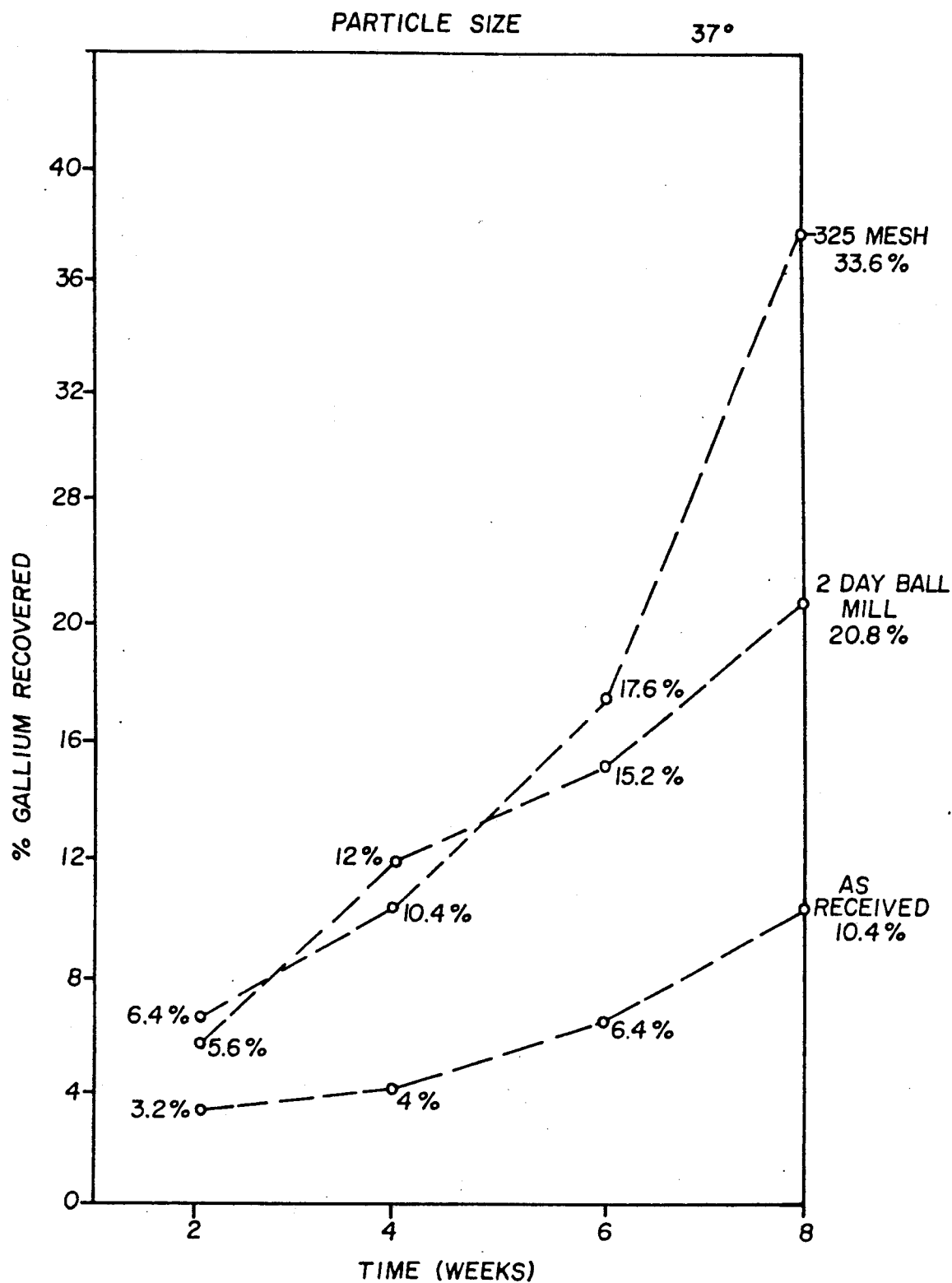
FIG. 1 is a graph comparing the relative effects of decreasing ore particle size on gallium recovery in a 37° centigrade(° C.) system.

Bacteria capable of bioleaching gallium and germanium from ores at elevated temperatures should be common, naturally occurring, and readily discoverable. Such strains would be thermophilic or mesophilic microorganisms. A thermophile is an organism capable of living at temperatures at or near the maximum for the taxonomic group of which it is part. Bacteria which grow at high temperature (above 40° C.) are classified as thermophiles, those growing at medium temperatures (20° to 37° C.), as mesophiles, and those which can grow at temperatures down to −10° C. as psychrophiles. Thermophilic microorganisms are widely distributed in soils, mine tailings, self-heated hays, and geothermally heated areas (e.g. tectonically active areas of the earth, sulfatara fields, and geothermal power plants). Mesophiles are also widely distributed throughout nature.

Once a source of mesophiles or thermophiles has been identified, various strains of the bacteria can be isolated using well-known techniques. For example, the bacteria may be streaked onto a sterile glass petri dish containing solid or semi-solid nutrient medium. This medium contains nutrients which the bacteria can use as food.

Within a few days, the various bacterial cells should reproduce covering the medium with colonies of bacteria. Assuming individual cells were well separated in the initial streaking, isolated colonies will have arisen from a single bacterium and will therefore be composed of many identical organisms.

If such a colony is touched with a sterile needle and the adhering cells transferred to another sterilized medium, the bacteria will reproduce as a pure culture (a culture composed of one kind of bacterium).

Other well-known pure culture techniques such as "streak-plate" or "pour-plate" (Example C) methods may be used to obtain pure cultures. The bacteria may also be sustained on a liquid medium such as infusion media. Infusion media is especially preferred for use with thermophilic bacteria due to the temperatures involved.

Preferably the medium will contain gallium, germanium, arsenic or mixtures thereof. In such a case, the medium can be used as a preliminary screening step to determine if the bacteria is capable of withstanding gallium, germanium, or arsenic concentrations. In the case of bacteria ATCC 53921, the concentration of arsenic in the medium should not exceed 13 weight percent.

Once the bacteria have been isolated into a pure culture, and preliminarily screened with gallium, germanium, and/or arsenic containing medium, the bacteria can be further screened to determine whether or not it can be used to bioleach the gallium or germanium from the ore. One such screening technique is to incorporate the isolated bacteria into the processes of the hereinafter described Examples A-C and then analyze the culture medium for the presence of the desired metal component.

A preferred bacteria for use in the instant invention is one deposited with ATCC which bears ATCC Deposit No. 53921. Bacteria ATCC 53921 was deposited with the American Type Culture Collection, 12301 Parklawn Drive, Rockville, Md. 20852, USA, under the Budapest Treaty on June 26, 1989. This bacteria bioleaches gallium arsenide at temperatures ranging from 15° C. to 90° C. Temperatures above 60° C. are preferred. At 62° C. the rate of bioleaching is five times faster than at room temperature. Generally, the greater the temperature, the greater the speed of the bioleaching with bacteria ATCC 53921.

Figure 12:
FIG. 12 is a photograph of a transmission electron microscopy scan of bacteria ATCC 52321 taken at 30,000 magnification.

Although not completely understood, bacteria ATCC 53921 appear to be pleomorphic organisms. At temperatures less than 65° C., bacteria ATCC 53921 appear to be gram positive cocci. At temperatures greater than 65° C., some of the organisms appear to change morphology to gram negative rods. Bacteria ATCC 53921 have some Sulfolobus characteristics (see e.g. FIG. 12) and are not of the genus thiobacillus or Leptobacillus. Since the addition of yeast extract to other culture medium accelerates the bioleaching process, bacteria ATCC 53921 are believed to be facultative heterotrophs in addition to thermoacidophilic autotrophs. The size of a bacterium of bacteria ATCC 539231 varies from 0.7 to 1.0 microns.

"Mutants" as used herein refer to bacteria which have mutated, either naturally, or by inducement (e.g. through exposure to ultra violet light). "Recombinants" as used herein refer to recipient cell forms into which the genetic material of a donor cell (e.g. bacteria ATCC 53921) has been placed. Processes for inducing mutations and creating recombinants can be found in various publications, such as Watson et al. *The Molecular Biology of the Gene*, Vol. 1 3–585 (W. A. Benjamin, Menlo Park, CA 4th ed. 1987) (mutations), Beers et al. *Cell Fusion: Gene Transfer and Transformation*, pp. 79–275 (Raven Press 1984); Denniston et al., *Recombinant DNA*, pp. 109–290 (Bowbin, Hutchinson, Strasburg, PA 1981); Chafer et al. *Genetic Rearrangement*, pp. 59–74 (Sinauer Assoc. 1980); and Kushev, *Mechanisms of Genetic Recombination*, pp. 5–175 (Consultants Bureau 1974) the contents of all of which are incorporated by this reference.

Bacteria, such as bacteria ATCC 53921, may be placed in the following media: ATCC-B, ATCC-D, ATCC Sulfolobus medium (pH adjusted to 2.0 with $H_2SO_4$), Nutrient Broth, Tryptone Glucose Extract, Sulfolobus medium (Brierley), Potato Dextrose, Lundgren's 9K and Silica Gel. Such media were prepared with 0.2 μm Nanopure ™ purified water in 500 or 1000 ml volumetric flasks. After diluting to volume, the flasks were heated slowly on a Corning hot/stir plate while stirring. After the ingredients were in solution or well dispersed, the media, excluding 9K, were autoclaved. The 1000 ml solutions were poured into 500 ml flasks due to autoclave size limitations. The flasks were autoclaved at 121.C/15 psi (pounds per square inch) for 20 minutes. Initial autoclaving was completed in 20 minutes. Sterilization times exceeding 15 minutes are preferred.

Typical formulations of such mixtures are:

A. ATCC-B

| Nutrient | % |
| --- | --- |
| Yeast Extract | 0.40 |
| Starch | 0.50 |
| Magnesium Sulfate | 0.05 |
| Potassium Dihydrogen Phosphate | 0.10 |
| Ammonium Nitrate | 0.10 |
| Sodium Chloride | 0.01 |
| If used for plates: | |
| Agar | 1.75 |

The solutions were pH adjusted to 5.5 with 1.0 N $H_2SO_4$ autoclaved.

B. Nutrient Broth

| Nutrient | % |
| --- | --- |
| Beef Extract | 0.30 |
| Peptone | 0.50 |
| If used for plates: | |
| Agar | 1.75 |

The solution was then diluted to volume, pH adjusted to 7.0 and autoclaved.

C. Tryptone Glucose Extract (TGE)

| Nutrient | % |
| --- | --- |
| Beef Extract | 0.30 |
| Tryptone | 0.50 |
| Glucose (Dextrose) | 0.10 |
| If used for plates: | |
| Agar | 1.75 |

The solution was then diluted to volume, pH adjusted to 7.0 and autoclaved.

Nutrient Media

D. Potato Dextrose

| Nutrient | % |
| --- | --- |
| Potatoes | 30.00 |
| Dextrose | 2.00 |
| If used for plates: | |
| Agar | 1.75 |

Diced potatoes were boiled in water until thoroughly cooked. The liquid and solids were then filtered through cheesecloth. The filtrate was placed in a volumetric flask with 2% dextrose diluted to volume and autoclaved. The solution was not pH adjusted and was used only for culture isolation.

E. 9K with Yeast Extract

ATCC 53921 bacteria were also maintained in Lundgren's 9K nutrient modified by the addition of yeast extract. This is the preferred culture medium. This pH 8 nutrient solution is a sterile filtered mixture of the following materials:

| Nutrient | Grams per Liter |
| --- | --- |
| Ammonium Phosphate | 0.3 |
| Potassium Chloride | 0.1 |
| Potassium Orthophosphate, mono-H | 0.5 |
| Magnesium Sulfate Heptahydrate | 0.5 |
| Ferrous Sulfate Heptahydrate | 45.0 |
| Calcium Nitrate | 0.01 |
| Yeast Extract | 0.1% |

F. Silica Gel Media

Three solutions were prepared. The first solution involved dissolving 10 g of silica gel into 100 ml of 7% w/v KOH. The solution was stirred on a hot plate until the silica gel was dissolved. The opaque, light tan liquid was then autoclaved at 121° C./15 psi for 20 minutes. The liquor was clarified. The second solution was a double strength concentration of 9K. This solution was pH adjusted to 1.8 with 1.0N $H_2SO_4$ and then sterile filtered through a Gelman Acrodisc TM 0.2 $\mu$m membrane. The third 20% o-phosphoric acid solution was prepared by diluting 85% certified o-phosphoric acid with 0.2 $\mu$m purified water. This solution was also sterile filtered through a Gelman Acrodisc TM 0.2 $\mu$m membrane. The medium was readied by adding 20 ml of the double strength 9K to 20 ml of the silica gel/KOH solution. After this addition, the ferrous sulfate precipitated out of solution. Approximately 2.5 ml of the 20% o-phosphoric acid solution was then added until the pH adjusted to 7.0. Petri dishes were poured and allowed to solidify.

Plate and Broth Preparation

After autoclaving, the flasks were again placed on the Corning hot/stir plates and stirred. Petri dishes were then removed from sterile plastic holding sleeve(s) and stacked by fours. Approximately 15 to 20 ml of hot agar was poured into each dish as the lids of the dishes were quickly raised. The lids were then replaced. After pouring agar into all dishes, each plate lid was again raised while a Bunsen burner flame was passed quickly over each agar surface to pop any bubbles. The plates were then allowed to cool. After cooling and setting of the agar, the lids were lifted and the water on the inside was shaken off. The plates were then allowed to dry completely before inoculation or return to the plastic sleeves.

A 10 $\mu$l pre-sterilized Elkay (Fisher 13-075-1) plastic loop or a 10 ml sterile pipette was used for culture inoculation and streaking of flasks and petri dishes. In streaking, the loop was dipped into an inoculating broth culture which had been well-stirred. When the test involved a broth, the loop was placed in the liquid and shaken vigorously into the new medium whereas when the experiment involved petri dishes, the loop was drawn across or "streaked" through the sterile agar, along one side of the dish. Another streak was then made through the first streak with another clean, sterile loop. This loop was then rotated 180° exposing a sterile surface, and zig-zagged through the second streak. For inoculation, a similar technique was used.

Since a fungal contaminant was shown to inactivate bacteria ATCC 53921 at room temperature, the culture media may also contain antifungal agents to prevent growth of the fungus. Such agents are well known to those skilled in the art and include both fungicidal and fungistatic agents, including potassium iodide.

The gallium- or germanium-containing host material or ore (e.g. jarosite, geothite, limonite, hematite, etc.) is preferably first crushed, comminuted or otherwise broken down into smaller pieces or particles. Generally the smaller the size of the crushed ore the greater the amount of desired metal compound extractable during the process.

For example, it has been found that the speed of oxidation increases in proportion to its degree of comminution up to $-400$ mesh. It was noted that large lumps of ore require extended periods to leach. Extraction is apparently partially dependent upon the amount of surface area available per unit volume. In shaker flask tests, the highest gallium extraction rates were obtained from the smallest particle size ($-325$ mesh) and largest surface area. As the particle size decreases and surface area increases, extraction rises to a maximum. FIG. 1 shows this trend in a 37° C. system. If the particles are finely ground in the beginning, the leaching rate is more rapid. The leaching rate is also apparently independent of the quantity of mineral present.

Experiments were conducted on the efficacy of leaching greater concentrations than the standard 10% solids. At low slurry density the speed of extraction and the rate of growth of the bacteria seems to be limited by the amount of energy producing material. At higher temperatures, the speed of extraction seems to be limited by the oxygen availability. The speed of extraction is also dependent upon the amount and kind of mineral salt available for bacterial intake.

Tests were run with 20% and 40% solids. Leaching, at the higher concentrations, was found to proceed at a slightly higher rate but the initial lag period was longer.

After comminution the ore is placed into a container containing culture medium inoculated with a bacteria capable of extracting the desired metal compound such as bacteria ATCC 53921. A concentration of bacteria sufficient to leach the metal compounds (e.g. 5cc of existing culture bacteria ATCC 53921 may be added to 200 ml of the hereinafter described 9K with gallium-containing ore) should be present in the culture medium, although the bacteria will eventually multiply in suitable culture medium to sufficient numbers to achieve bioleaching. Bacteria ATCC 53921 generally attach to the crushed metal-containing ores immediately. Gallium compound dissolve into the culture medium, along with germanium compounds.

The particular culture medium containing the bacteria and crushed ore is preferably mixed during the bioleaching process. A magnetic bar stirrer works ideally. Such mixing or agitation increases the gallium compound distribution throughout the solution.

After the desired metal compound has been extracted from the ore and dissolved into the culture medium, the culture medium is filtered or otherwise separated from the other constituents.

Figure 13:
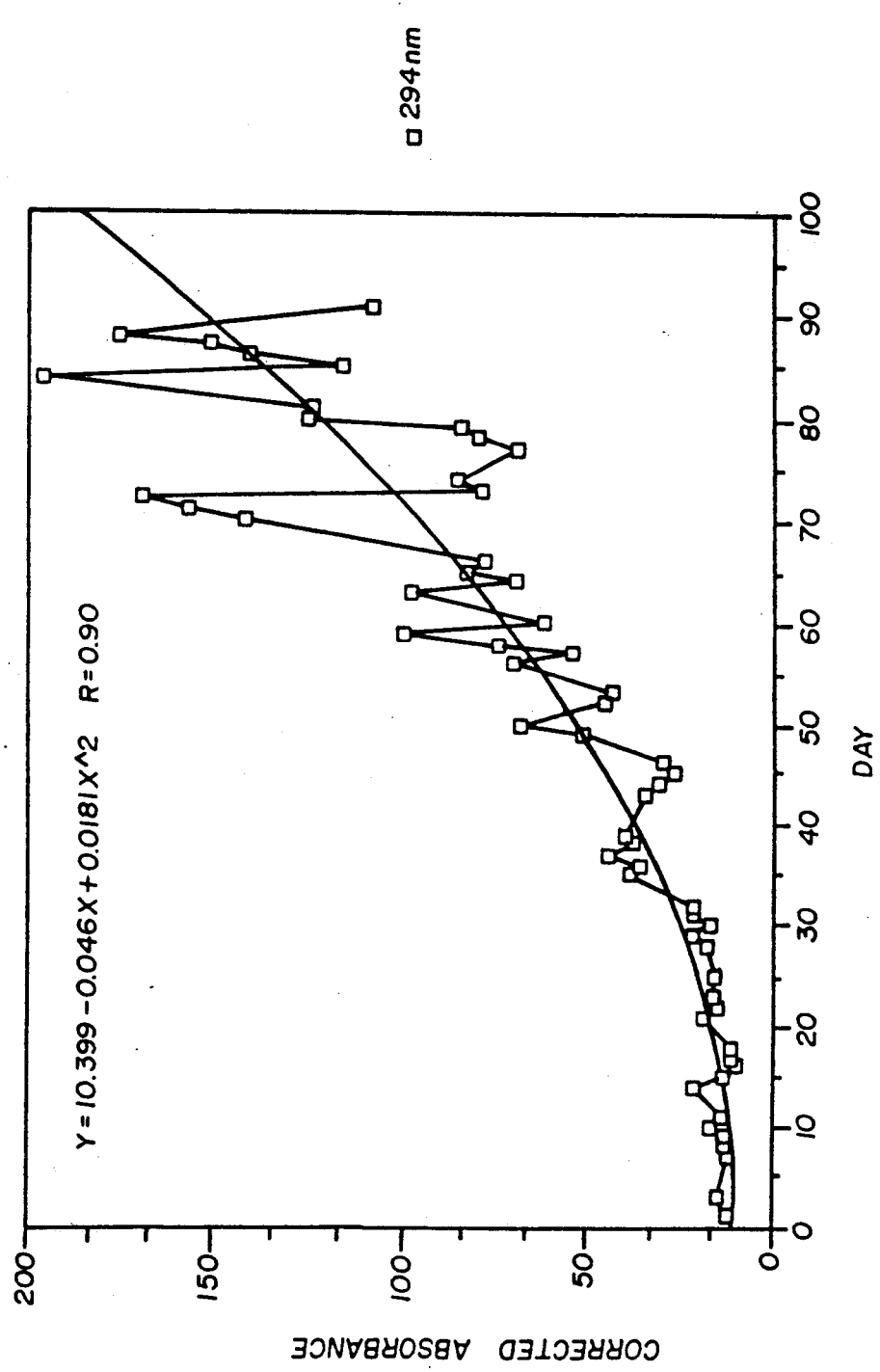
FIG. 13 depicts the amount of gallium (wavelength = 294 nm) leached into liquor over time during a bioleaching process using bacteria ATCC 53921.
Figure 14:
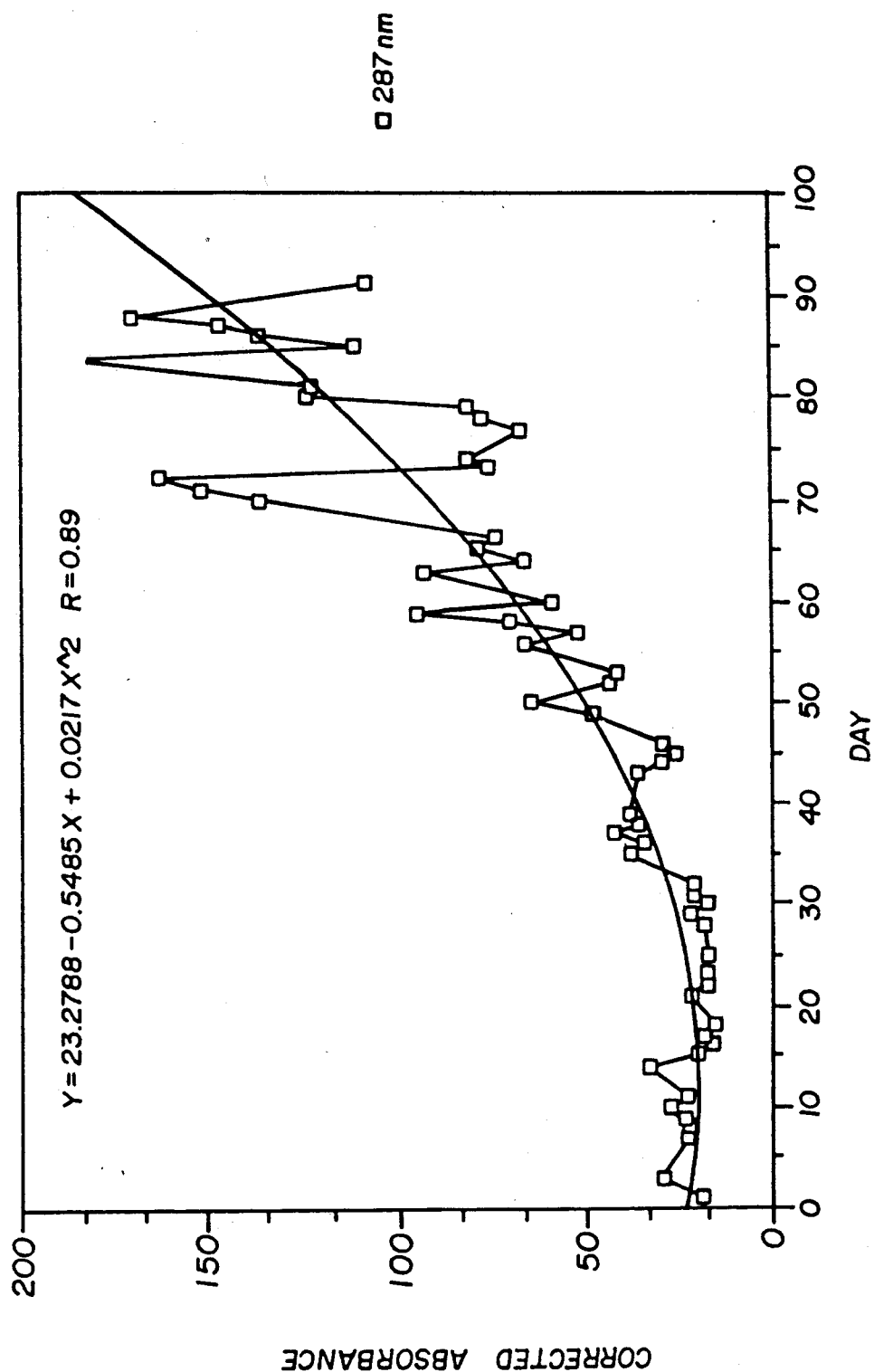
FIG. 14 is a graph depicting the amount of gallium (wavelength = 287 nm) leached over time during a bioleaching process using bacteria ATCC 53921.

The gallium or germanium is then recovered from the culture medium using one of several known extraction techniques (e.g. ion exchange, biosorption, accumulation, or bioaccumulation). See, e.g. "Development of a Continuous Process for Metal Accumulation by *Zoogloea ramioera*" by Norber, et al. (26 *Biotech and Bioeng.* 1984, pp. 265–68) which discusses bioaccumulation of metals from aqueous solutions; "Biosorption of Uranium and Lead by *Streotomyces Longwoodensis*" by Friis, et al. (28 *Biotech and Bioeng.* 1986, pp.21–28) which discusses the recovery of heavy metals through the mechanism of biosorption; "Accumulation of Heavy-Metal Ions by *Zoogloea ramigera*" by Norberg, et al. (26 *Biotech. and Bioeng.* 1984, pp. 239–46) which describes a method for accumulation of metals from effluent solutions using bacteria; "Bioaccumulation of Germanium by *Pseudomonas putida* in the Presence of Two Selected Substrates" by Chmielowski, et al. (*Applied and Envir. Microbiology*, May 1986, pp. 1099–103) which discusses the recovery of germanium from the wastewaters of coke technology by bioaccumulation; the chemistry and detection of gallium using calorimetric methodology is disclosed in "The Separation of Gallium and its Calorimetric Determination by Means of Quinalizarin" by H. Willard, et al (1937); and "*The Chemistry of Gallium*" by Sheka, et al. (Elsevier Publishing Co. 1966) presents a compendium of gallium chemistry, and discusses the recovery of gallium in the aluminum industry using solution leaching processes and other methods. The publication "Analytical Chemistry of Gallium" by Dymov and Sarostin (Ann Arbor Science Publishers, 1970) discusses the characteristics and properties of gallium, and discusses various methods of extracting gallium including electrical extraction, chromatography, and the use of organic solutions. The contents of these references are hereby incorporated by this reference Example A Bioleaching of gallium and germanium is accomplished by seeding a bioreactor with 10% bacterial culture of bacteria ATCC 53921 acclimated on a 10% solids raw material input. A nutrient (9K) is added for initial growth. The ore for leaching is ground to between 20 and −400 mesh, and is placed within the nutrient solution. Reaction temperatures range from between 25° and 85° C., with an optimum temperature of about 62° C. to 72° C. Filtered deionized water ($>0.2$ microns), pH 1.8, is added to off-set water loss due to evaporation. The treated solution is later analyzed for the presence of gallium and germanium, which are detected along with zinc, tin, lead, copper and arsenic. FIGS. 13 and 14 depict the ultra violet absorbance of a bioleaching liquor at 294 and 287 nanometers, respectfully, over time. The bioleach liquor (culture medium containing bacteria ATCC 53921) was analyzed with a Milton Roy Scanning Spectrophotometer. The amount of absorbance directly corresponds to the amount of gallium present in the liquor.

Example B

I. Apparatus

The experiments were conducted in a microbiological laboratory with a controlled 25° C. temperature room. All experiments were carried out in 250 ml Erlenmeyer flasks containing active bacteria (ATCC 53921) (except controls), nutrient medium, and the desired quantity of substrate.

Figure 2:
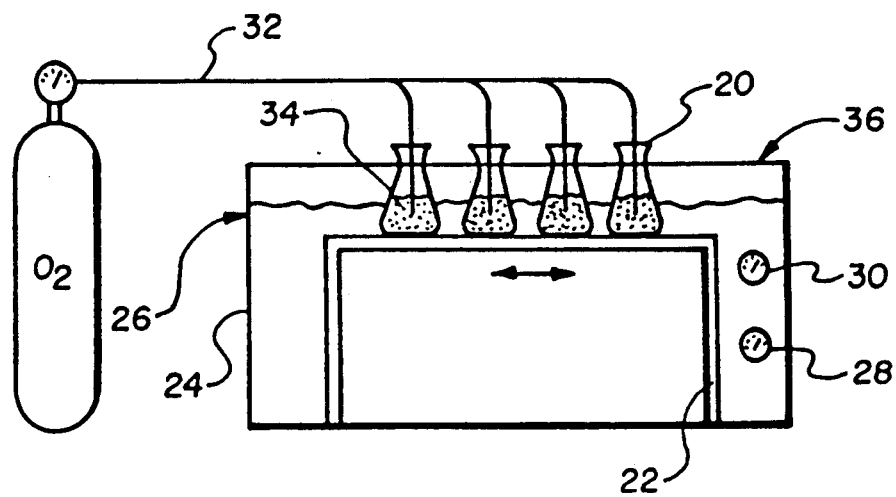
FIG. 2 depicts an apparatus used in Example B.

The 25° C. experiments were placed on Thermolyne stirrers and aerated. An Eberbach shaker water bath was set up for the 75° C. experiments (FIG. 2). The shaker-flask system was reported to be an effective laboratory scale leach technique found to simulate the mechanical mixing of a unit volume of water with a unit volume of material.

As depicted in FIG. 2 this water bath apparatus has Erlenmeyer flasks 20 placed upon a horizontally moving support and shaker plate 22 within a container (bath) 24 of water at water level 26. The water temperature is monitored by means of a thermometer 28, and the temperature regulated by a thermostat 30 in conjunction with heating coils (not shown). Oxygen may be diffused through conduit 32 bubbled through the reaction mixture 34 of ore, bacteria and nutrient media. A speed bar 36 may be optionally used.

Figure 3:
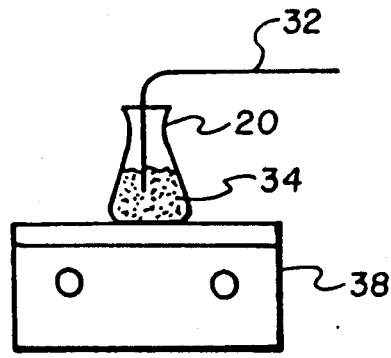
FIG. 3 depicts another apparatus used in Example B.
Figure 4:
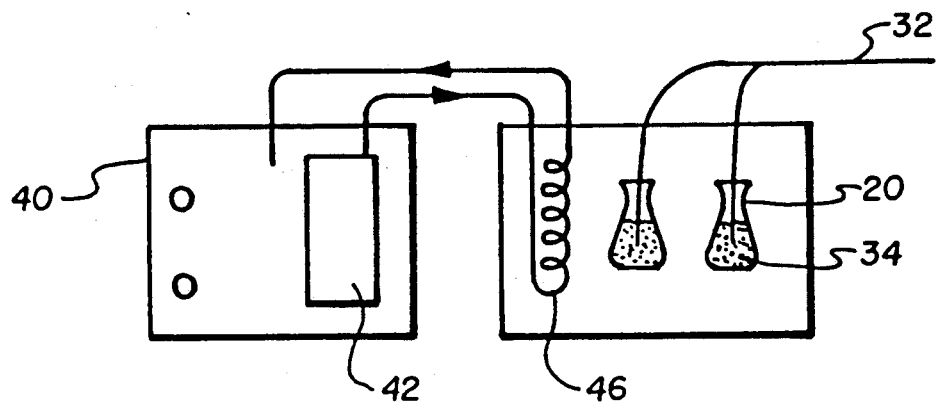
FIG. 4 depicts another apparatus used in Example B.

Tests were also conducted on a Corning combination stirrer/hot plate 38 at 75° C. (FIG. 3) with a Teflon magnetic stir bar (not shown) placed in the nutrient media 34 within the flask 20. Another water bath system (FIG. 4) was set up for the 37° C. temperature runs. FIG. 4 depicts the heater water bath 40 with pump 42 passing heated water through a conduit 44 to heat transfer coil 46. pH corrected distilled water was added periodically to compensate for water loss due to evaporation both in flasks and water baths.

A Gast pressure/vacuum pump was used to aerate those flasks not aerated by pure oxygen or carbon dioxide. A filter was placed in the oxygen, carbon dioxide, and air lines with a trap to prevent contamination from pump oil and other bacteria.

A Gelman filter apparatus and Serval angle centrifuge were used to separate samples for analysis. An Ohaus micrometer scale measured solid weights. The liquor was analyzed for its metal content with an atomic absorption (AA) spectrophotometer and inductively coupled plasma (ICP). The leach residue was analyzed with X-ray diffraction, LECO sulfur analyzer and AA. The pH was analyzed with a Sargent-Welch specific ion analog meter.

Incubators set at 37° C. and 75° C. were used to culture the bacteria for morphologic and metabolic characterization. An autoclave was set at 121.5° C. and fifteen pounds pressure. Nikon, Olympus and Leitz microscopes and JEOL model JSM 35 scanning electron microscope (SEM) with Kevex 7000 were used for bacterial analysis and photography.

II. Materials

Fifty pounds of representative ore were taken from the Apex mine. Of this 50 pounds, 350 grams were used in these experiments. The ore analysis indicated weight percents of Fe, 14.8%; Cu, 1.5% Zn, 1.65%; Ge, 0.092%; Ga, 0.042%; As, 1.11% and Ag, 2.2 oz. troy.

ICP results were as follows:

| Elements | ICP Wt. % | Element | ICP Wt. % |
|---|---|---|---|
| Ga | 0.043 | Mg | 1.070 |
| Ge | 0.070 | Mn | 0.010 |
| Ag | 0.030 | Mo | 0.050 |
| Al | 0.250 | Ni | 0.030 |
| As | 1.610 | Na | 0.150 |
| Au | <0.010 | Pb | 3.900 |
| Ba | 0.020 | Sb | 0.130 |
| Bi | 0.050 | Si | 0.060 |
| Ca | 2.260 | Sn | <0.010 |
| Cr | <0.010 | U | 0.050 |
| Cu | 0.940 | V | <0.010 |
| Fe | 20.600 | Zn | 1.140 |

Lundgren's 9K and O'Connor's nutrient were chosen as growth medium.

O'Connor's medium was made with equal molar volumes of urea and phosphoric acid. The medium required a 1 gram per liter dilution. Both solutions were made with autoclaved double distilled water.

Carbon dioxide and oxygen were supplied by A-L Welding Products, Inc. of Salt Lake City, Utah. Chemicals and glassware were purchased from Fisher Scientific. Distilled water was supplied by Culligan.

III. Procedure

A representative sample of 220 grams of Apex mine ore was milled with 2000 grams of ¼ inch diameter stainless steel balls in water for two days to begin initial tests. The Tyler sieve analysis was as follows:

| Tyler Mesh | Unground Ore (wt. %) | Ground Ore (wt. %) |
|---|---|---|
| 65 | 71.95 | 62.85 |
| 100 | 4.57 | 8.89 |
| 140 | 5.08 | 7.21 |
| 200 | 5.81 | 9.18 |
| 270 | 2.37 | 3.73 |
| 325 | 1.80 | 1.78 |
| −325 | 8.43 | 6.38 |

100 grams of the ball milled ore, sterilized at 70° C. for 1 hour, were added to a 100 ml aliquot of a bacterial slurry containing bacteria ATCC 53921 in an intermediate solution consisting of 1 liter Lundgren's 9K medium (autoclaved at 121.5° C. for 15 minutes and 15 pounds pressure and pH adjusted to 1.8) in order to acclimate the bacteria to the Apex ore. The solution was mechanically agitated on a stir plate and aerated with house air. Sulfuric acid buffering with occasional ferrous sulfate addition was required due to a consistent rise to pH 4. The intermediate acclimation was complete when the pH stabilized at 1.5 and the larger ore particles had been incorporated into a homogenous slurry.

Once the intermediate acclimation was complete, 5 ml of the resulting bacterial culture, 95 ml nutrient medium and the desired quantity of substrate were placed in the 250 ml Erlenmyer flasks to begin the tests. The flasks were placed in the shaker bath, water bath, or on the heated stir plates. Sterilized controls (2.5% potassium dichromate in ethanol) were maintained for each variable throughout the study. The pH, temperature, agitation, gas flow where applicable, and water level were monitored daily and corrected when necessary.

The major difference in sample treatment was system temperature: 25°, 37°, and 75° C. The flasks within the temperature systems were separated into these groups:

1) bacteria: bacterial versus no bacterial addition (controls sterilized with 2.5% potassium dichromate in ethanol);
2) pH: 1.8, 4.5, 7.0;
3) nutrient medium: Lundgren's 9K, O'Connor, double distilled water, pyrite addition;
4) aeration: oxygen, carbon dioxide, house air, no aeration;
5) particle size: as-received, two day ball mill, −325 mesh;
6) percent solids: 10%, 20%, 40%

IV. Results

Bacterial and chemical solubilization depend upon many factors some of which are: nature of the ore, temperature and pH at which leaching occurs, availability of and use of nutrients, particle size of the material, slurry density, shape of the vessel in which the process is carried out, metal tolerance, water potential and surface tension, light and pressure. The following variables were studied:

temperature
pH
energy sources (9K, $O_2$, CO)
particle size
mineralogy

To determine the extent of, and optimize gallium bioleaching, an aliquot was removed every two weeks from each sample and replaced with a distilled water/nutrient medium. The first set of samples were separated by Gelman membrane filtration. Both the liquid and dried solids were analyzed. Filtration required from one-half to one hour per sample which proved inefficient. The higher temperature samples could cool during this time, requiring re-adaption. In addition, dissolved solids were not adequately washed into the liquor, preventing accurate analysis. As a result, centrifugation was used to separate liquor from solid material in the latter third of the project. Project results are as follows:

A. Temperature

An increase in temperature in a system increases the rate of all the reactions involved in growth. The optimum temperature for growth is defined loosely as that temperature above which the damaging reactions just produce a discernible effect. The maximum temperature is that at which the rates of damaging reactions become equal to those of the metabolic processes so that no growth takes place.

Bacterial growth can occur at any given point within the temperature range. At the lower end of the range, growth is very slow and the net synthesis of cell constituents may not occur. At higher temperatures, sufficient energy and precursors can be produced and accumulated to allow net synthesis, which is growth, at a rate that increases with temperature up to the optimum temperature. At temperatures above the optimum, heat-catalyzed degradation of essential cell constituents opposes their synthesis and activities, and the growth rate is lower.

Figure 5:
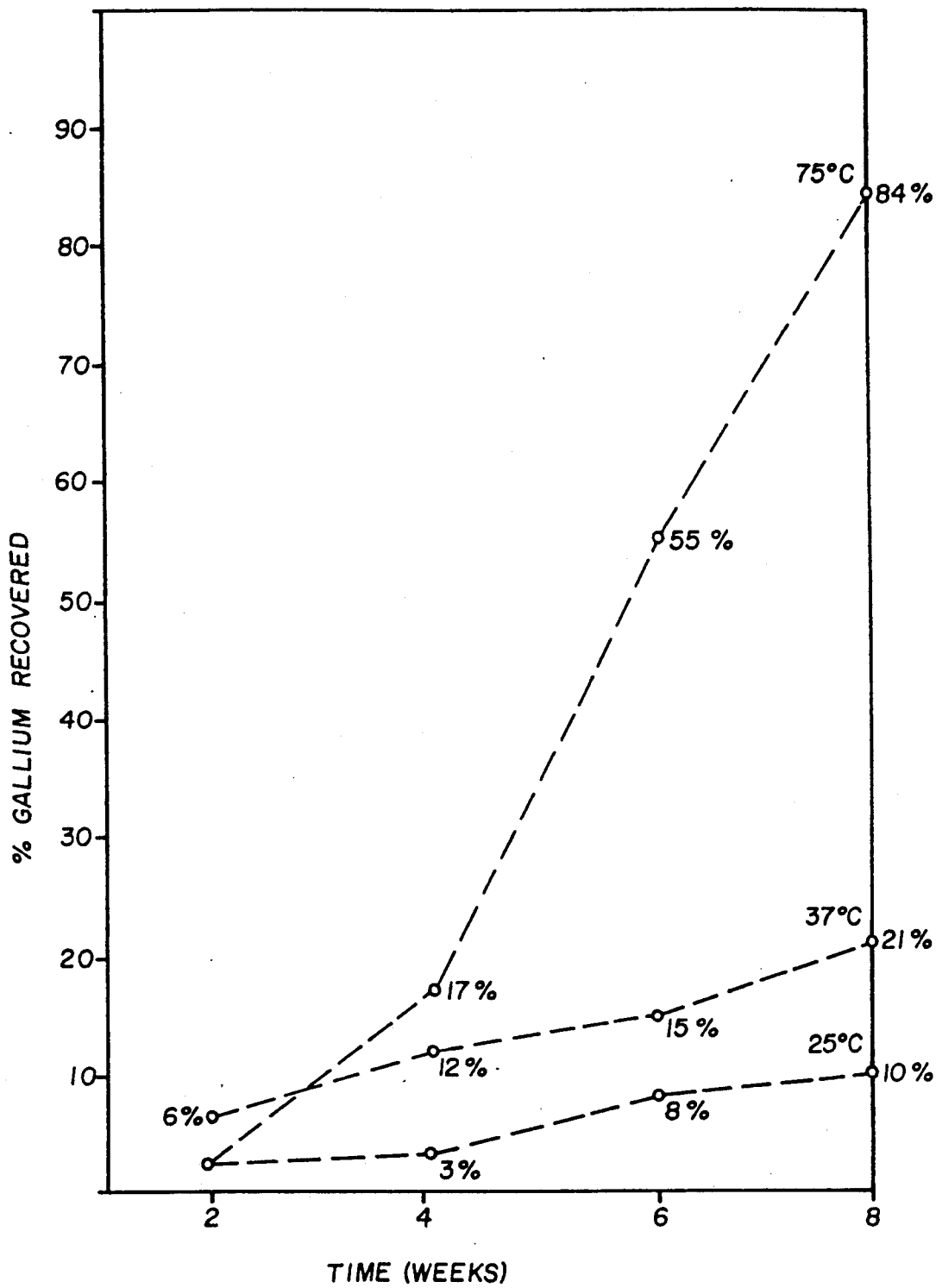
FIG. 5 is a graph comparing the percentage of gallium recovered with the process versus time for three different process temperatures (25° C., 37° C., 75° C.)

Three temperature profiles were run in these examples, two mesophilic and one thermophilic. Previous tests with this bacteria had shown effective solubilization at 37° C. FIG. 5 indicates that solubilization was greater at thermophilic conditions (75° C.) than mesophilic (both 25 and 37 degrees C).

B. pH

The acidity of the solution and its relation to bacterial activity on the ore is a major factor in bacterial leaching. The production of acid or alkali from the substrate by bacterial activity appears to enhance or limit growth.

Figure 6:
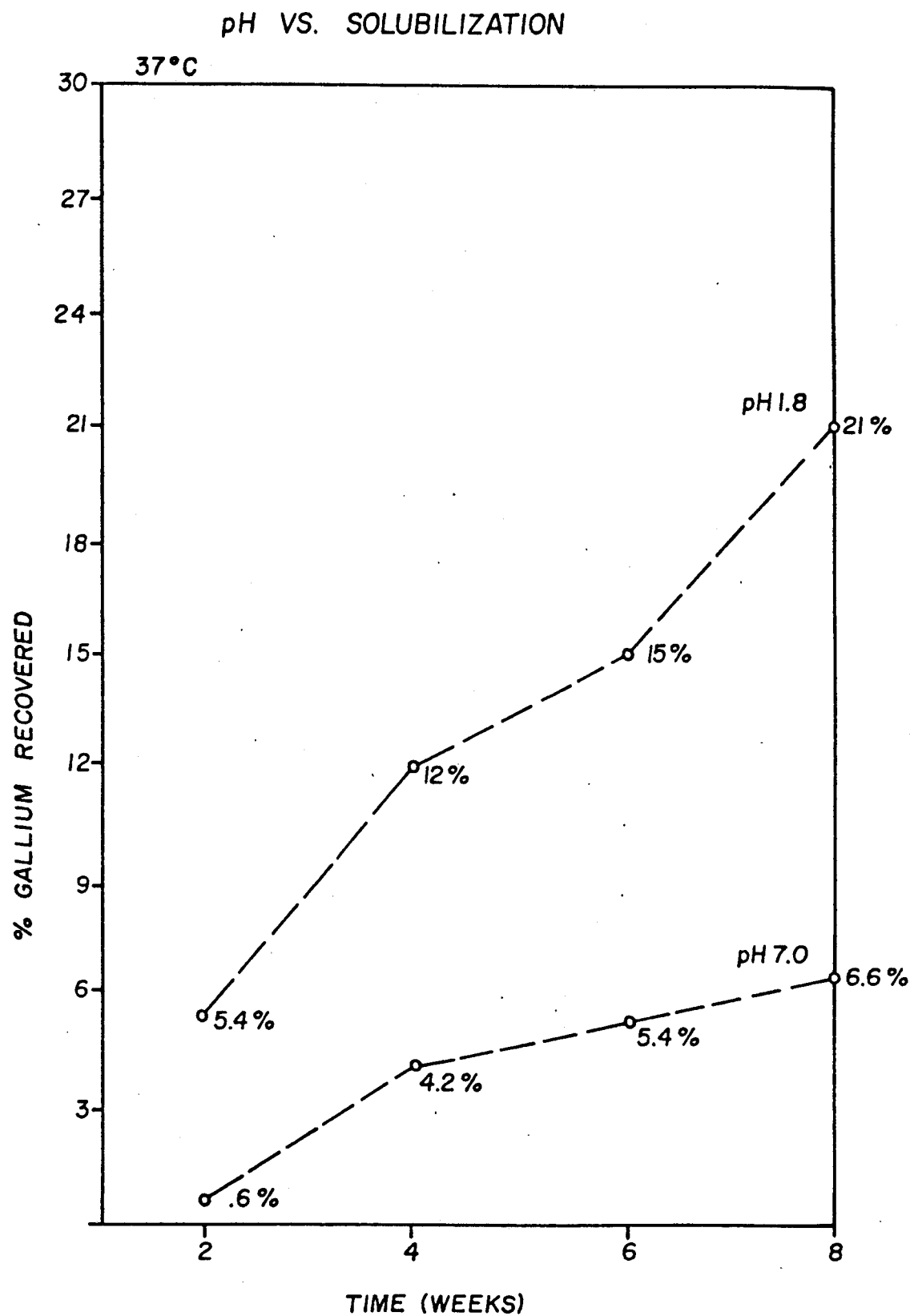
FIG. 6 is a graph comparing the percentage of gallium recovered over time for two different pH's (pH = 1.8 and pH = 7.0) at 37° C.

Once growth was initiated, this project examined maximum and minimum pH factors. The pH in FIG. 6 is plotted versus time and mineral solubilization in a 37° C. system. Buffering with sulfuric acid was initially required for samples below pH 2 because the host minerals, especially the limonite ($2FeO_3$), metal carbonates and oxides, increased pH when solubilized.

Previous work with bacteria ATCC 53921 showed that efficient solubilization occurred at pH 1.8. Therefore, pH values of 1.8, 4.5 and 7.0 were used in this project. With the Apex ore, pH greater than 2 slowed solubilization and pH greater than 5 inhibited and often killed the bacteria. The pH stabilized between 1.3-1.5 in the course of bacterial solubilization.

Figure 7:
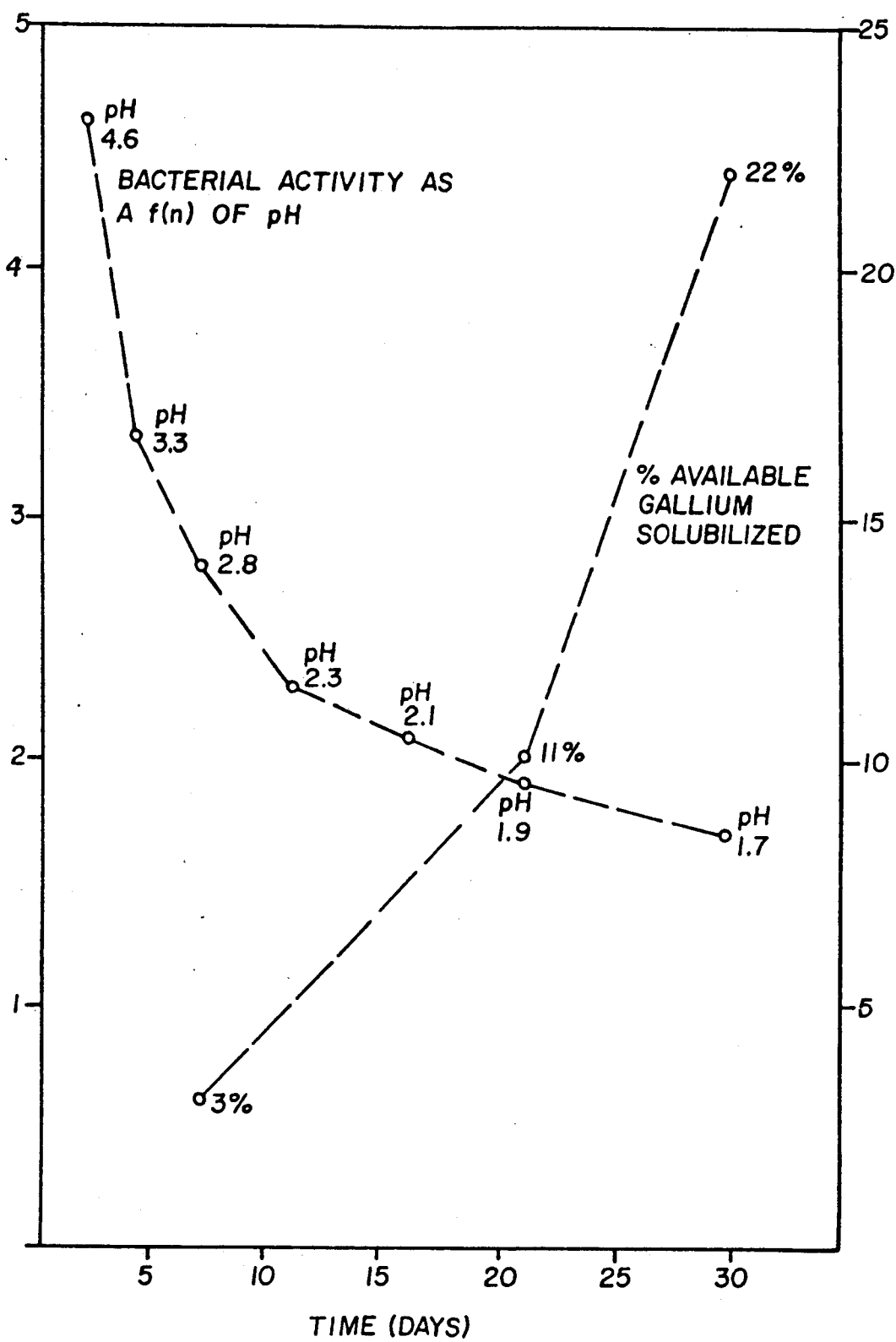
FIG. 7 is a graph depicting pH versus time (X-axis) on the left Y-axis and percentage available gallium solubilized on the right Y-axis at 37° C.

An additional experiment was run to determine the pH as a function of bacterial activity. The samples (with 9K nutrient, ball-milled ore, 10% solids) initially stabilized at pH 4.6. In two weeks the pH dropped to 2.1 and then to pH 1.7, within two days. Solubilization increased as pH decreased as shown in FIG. 7. Due to this finding it is believed that buffering agents will not be needed.

Experiments tried to pinpoint nutrients which encouraged bacterial growth and enhanced the bacterial leaching of the Apex gallium ore. Three systems were used to define medium addition: Lundgren's 9K, O'Connor's carbourea and sterilized (2.5% Potassium Dichromate in ethanol) double distilled water. All materials were autoclaved.

Figure 8:
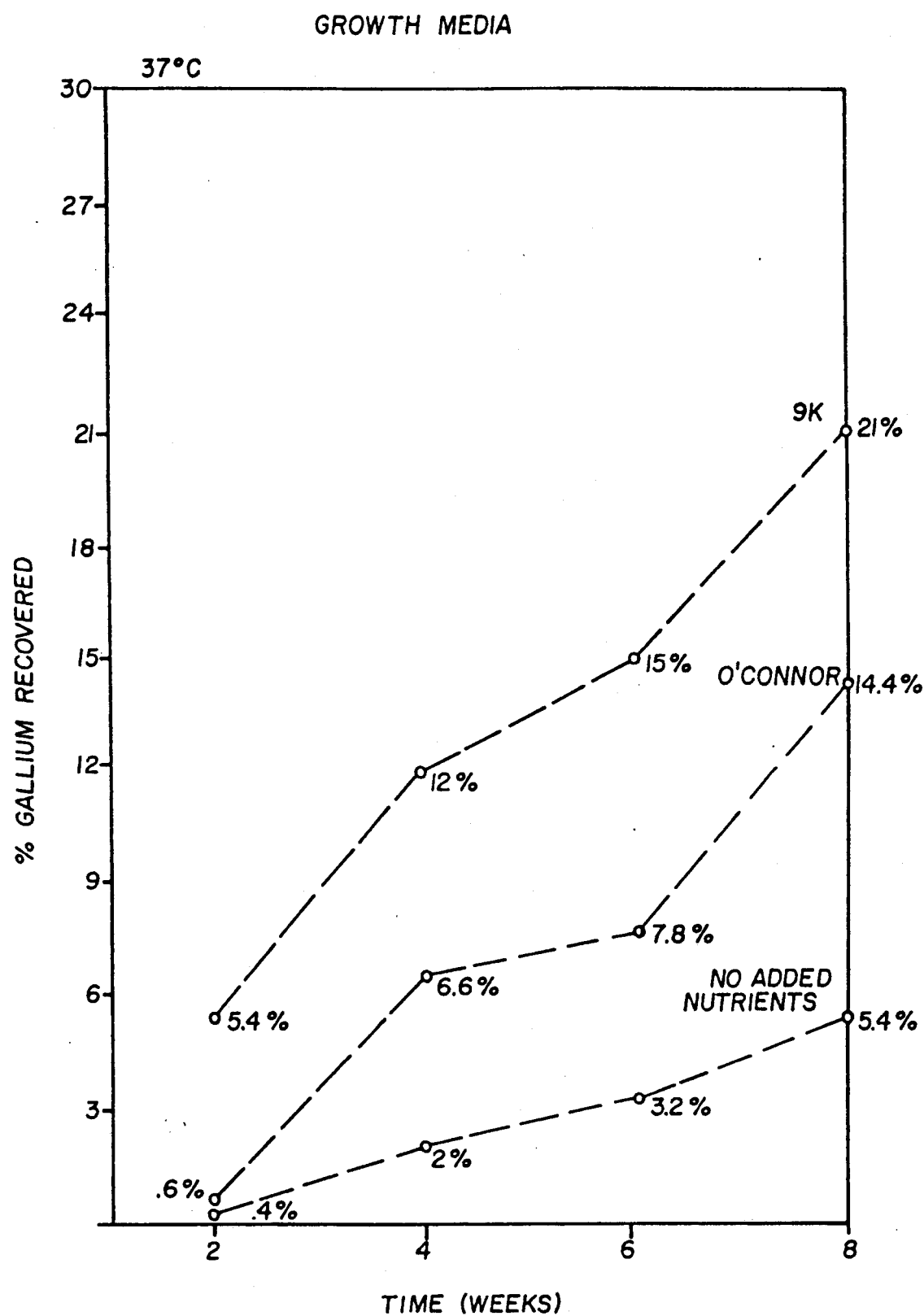
FIG. 8 is a graph depicting the percentage of gallium recovery using various nutrient media.

Nutrient addition was important for the efficient growth and activity of the bacteria. Lundgren's 9K medium was determined to be the optimum material studied. FIG. 8 depicts this nutrient trend in a 37° C. system. O'Connor's solution did not significantly increase material solubilization in comparison to nonnutrient.

Figure 9:
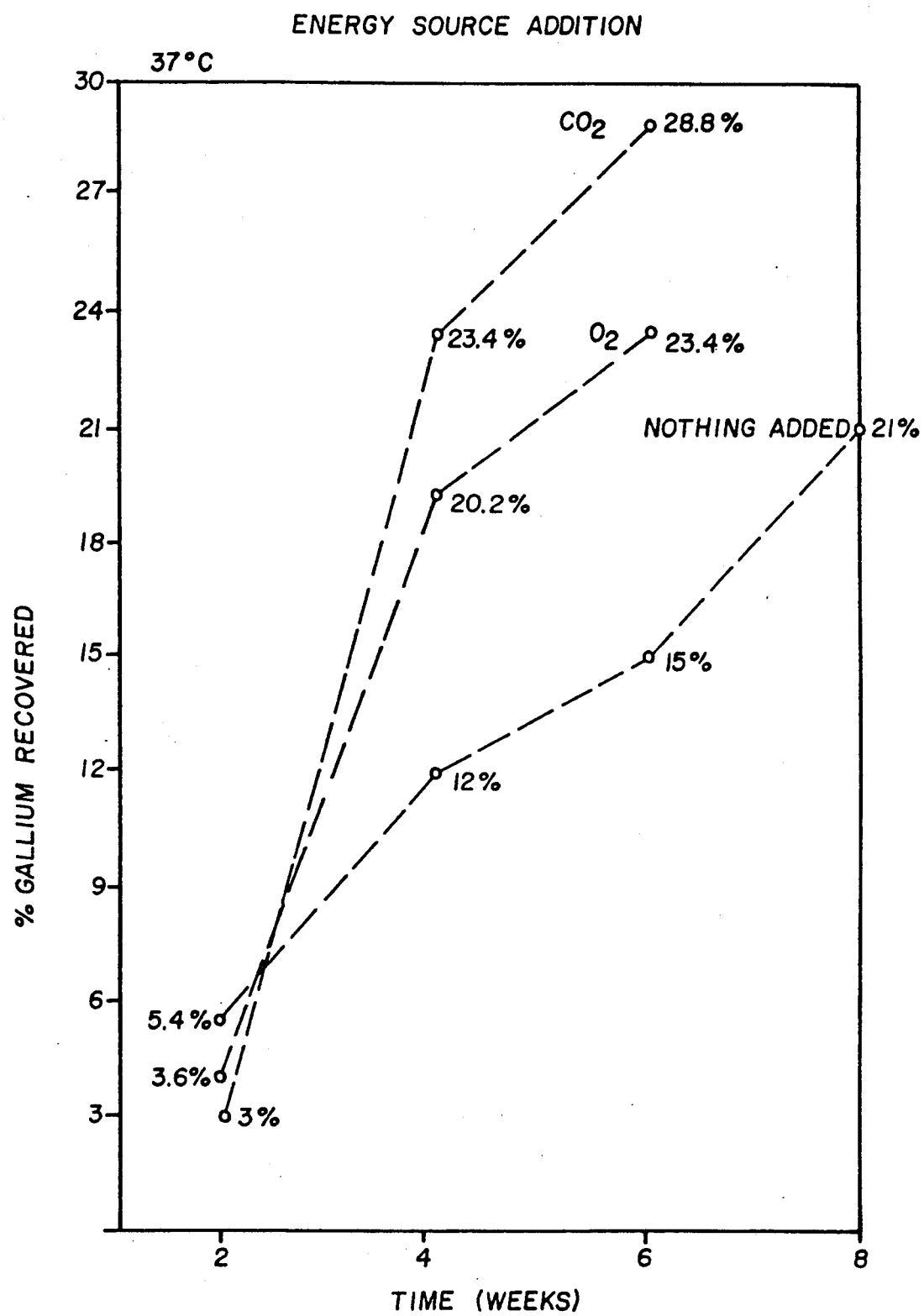
FIG. 9 is a graph depicting the effects of aeration on percentage gallium recovery at 37° C.

FIG. 9 indicates that oxygen availability did stimulate growth but that in this system the carbon dioxide was found to be the leach initiator, optimizing growth. The data is from a 37° C. system.

C. Bacteria

Cultivation of the bacteria has included agar, silica gel and broth systems. The agar and silica gel materials, however, dissociate under 1.5 pH and 75° C. conditions. The broth systems included tests with Lundgren's 9K nutrient, 9K with added yeast and 9K with added precipitated sulfur. An increase in turbidity was shown both in the 9K broth and 9K broth plus sulfur systems.

The inoculum was either taken directly from the sample slurry or a centrifuged liquor.

V. Conclusions

Figure 10:
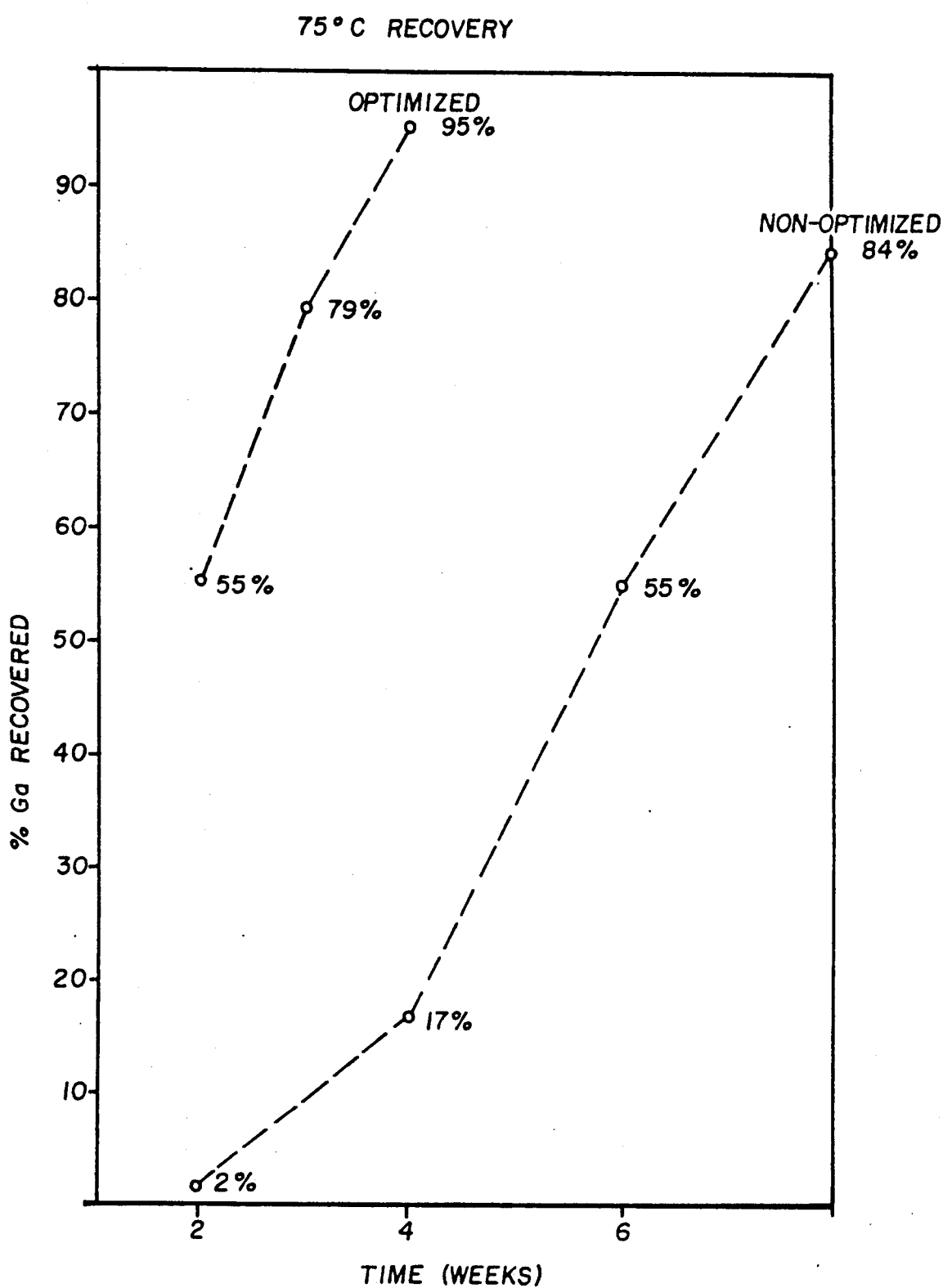
FIG. 10 is a graph depicting the percentage of gallium recovered under preferred conditions as disclosed in Example B.V.
Figure 11:
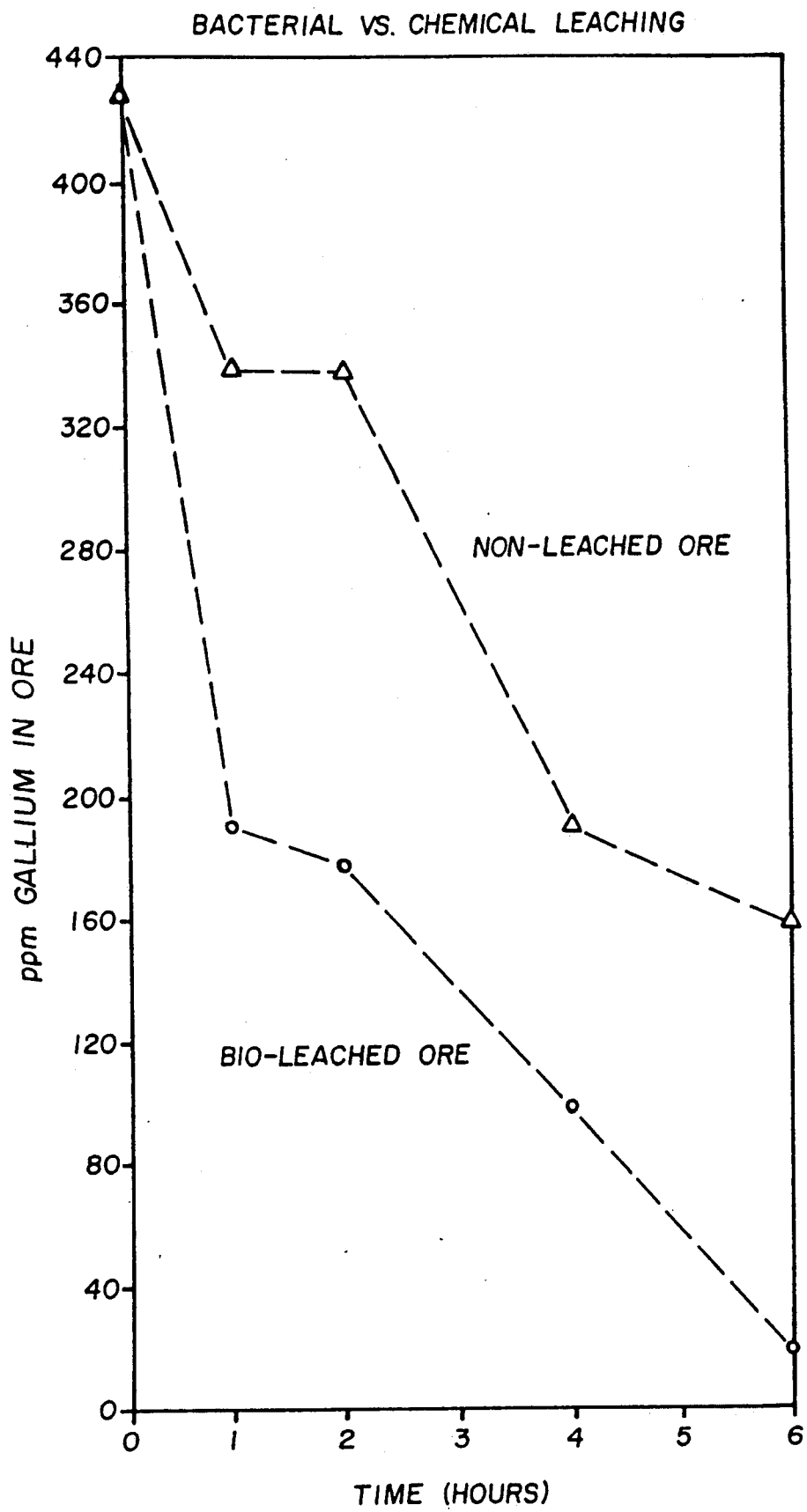
FIG. 11 depicts the parts per million (ppm) of gallium in ore versus time in bacterial and chemical leaching.

Bioleaching proved to be efficient in solubilizing gallium from the ore with a 95% removal in three weeks under optimum conditions (FIG. 10). The optimal conditions were:
Temperature: 75° C.
pH: 1.3-1.5
Agitation: vigorous
Nutrients: Lundgren's 9K and small amount $CO_2$
Particle size: −325 mesh A final experiment demonstrated biological leaching efficiency. A −325 mesh non-bioleached ore was tested concurrently with partially bacterially-leached solids. The Apex mine process uses an 85° C., 20% solids, 40% concentrated sulfuric acid chemical leach. The leaching conditions were:
Temperature: 70° C.
Agitation: vigorous
% Solids: 20
Chemical Leach Solution: 40% $H_2SO_4$/deionized $H_2O$ Tests were run in 250 ml Erlenmeyer flasks. Samples were collected 1, 2, 4 and 5 hours after leaching began. The flasks were brought to original weight before sampling by the addition of the distilled water/40% $H_2SO_4$ solution. An aliquot was withdrawn and the material filtered, washed and solids dried (FIG. 11). The new weight was noted and the flasks returned to the heated stir plates.

FIG. 11 shows that bacterial contact increased the efficiency of solubilizing the gallium. With less than 20 ppm gallium left in the ore, a greater than 95% recovery rate was established. The chemical leach left 150 ppm gallium in the non-bioleached material, yielding only a 65% recovery.

The small amount of sulfide in the ore retards the speed with which gallium can be removed. Pyrite addition of 1% yields a slight increase in solubilization but the appropriate additive ratio is not known. Pyrite is an inexpensive, easily available source of sulfide. Vitamin, yeast extract, amino acid, or trace mineral addition of 1% may also increase the rate of solubilization.

Oxygen aeration gave mixed results when added alone; when added with carbon dioxide, solubilization increased.

Example C

A soil sample taken at a geothermal power plant is used to inoculate a medium (e.g. the previously described Lundgren's 9K). The medium contains, dissolved therein, gallium sulfide and germanium sulfide (e.g. 5 weight percent) and is maintained at a temperature greater than 60° C. Mixed bacterial colonies are allowed to grow in this medium creating a mixed culture. This procedure preliminarily screens the mixed culture of bacteria and other microorganisms not able to withstand temperatures greater than 60° C. and concentrations of gallium and germanium.

The mixed culture is then diluted with sterile water using sterile techniques. The dilution of mixed culture is then immediately used to inoculate a test tube containing a melted agar medium that has been cooled to 45° C. The test tube is then agitated to disperse the organisms throughout the medium before being poured into sterile petri dishes and allowed to solidify. Alternatively, a liquid nutrient broth agar may be used. A culture from this method should result in evenly dispersed bacteria. Dilutions must contain enough organisms to provide a number of separate colonies on each plate without covering the petri dish with colonies that have grown together which may require several different dilutions to be plated.

Each of the separate colonies is then tested for its ability to bioleach the desired metals from the ore. Such testing may be done as previously described in Examples A-C, substituting the bacteria being tested for bacteria ATCC 53921.

Reference to specific embodiments or examples are not intended to limit the scope of the appended claims.

We claim:

1. A method of leaching a metal compound having a metallic component selected from the group consisting of zinc, tin, lead, gallium, germanium, or mixtures thereof from an ore containing said metal compound, said method comprising:

placing said ore into a liquor comprising an admixture of aerobic thermophilic bacteria and culture medium for sustaining the growth of said bacteria at temperatures greater than 50 degrees centigrade and for a sufficient amount of time to allow said bacteria to leach said metal compound from said ore, said aerobic thermophilic bacteria having deposit accession number ATCC 53921 and, having the ability to leach said metals from said ore, and having an affinity for arsenic.

2. The method according to claim 1 wherein said ore is crushed before being placed into the admixture of culture medium and bacteria and said liquor is maintained at greater than 50° centigrade.

3. The method according to claim 2 wherein said ore is a gallium and germanium host material, said host material selected from the group consisting of geothite, limonite, hematite, jarosite, azurite, malachite, conichalcite, and mixtures of any two or more of said group.

4. The method according to claim 2 wherein said ore is crushed to between 20 and −400 mesh.

5. The method according to claim 4 wherein the culture medium containing bacteria and ore is maintained at a temperature of about 62 to about 75 degrees centigrade.

6. The method according to claim 5 further including infusing carbon dioxide containing air through said liquor.

7. The method according to claim 6 wherein the liquor and ore is maintained at a pH of between 1.0 and 2.5 by addition of an amount of acid sufficient to lower the pH value of the liquor thereto.

8. The method according to claim 2 wherein said metal component of said metal compound is germanium of gallium.

9. The method according to claim 8 wherein said metal component is gallium.

10. The method according to claim 8 wherein said metal component is germanium.

11. A method of leaching gallium or germanium compounds from an ore containing gallium compounds, germanium compounds or mixture thereof, said method comprising: placing said ore into an admixture comprising a culture medium and bacteria having deposit accession number ATCC 53921 for a sufficient amount of time to allow said bacteria to leach gallium compounds, germanium compounds, or mixtures thereof from said ore.

12. The method according to claim 11 further including crushing said ore before placing the ore into the culture medium containing bacteria.

13. The method according to claim 12 wherein the culture medium is 9K with yeast.

14. The method according to claim 13 wherein said ore is crushed to between about 20 and about −400 mesh.

* * * * *